(12) United States Patent
Chen et al.

(10) Patent No.: US 9,291,607 B2
(45) Date of Patent: Mar. 22, 2016

(54) NANO-ANTENNA BASED INFRARED MOLECULAR TAGGANTS

(75) Inventors: Sung-Wei Chen, Las Vegas, NV (US); Christopher J. Rothfuss, Laramie, WY (US)

(73) Assignee: Empire Technology Development LLC, Wilmington, DE (US)

( * ) Notice: Subject to any disclaimer, the term of this patent is extended or adjusted under 35 U.S.C. 154(b) by 203 days.

(21) Appl. No.: 13/879,751

(22) PCT Filed: Aug. 14, 2012

(86) PCT No.: PCT/US2012/050744
§ 371 (c)(1),
(2), (4) Date: Apr. 16, 2013

(87) PCT Pub. No.: WO2014/028002
PCT Pub. Date: Feb. 20, 2014

(65) Prior Publication Data
US 2014/0205749 A1    Jul. 24, 2014

(51) Int. Cl.
*G06K 7/10* (2006.01)
*G01N 33/00* (2006.01)
*H01Q 1/22* (2006.01)
*G01N 33/58* (2006.01)

(52) U.S. Cl.
CPC .............. *G01N 33/00* (2013.01); *G01N 33/587* (2013.01); *H01Q 1/2225* (2013.01); *Y10T 436/13* (2015.01)

(58) Field of Classification Search
CPC ....... H01Q 1/2225; H01Q 15/00; H01Q 1/38; H01Q 1/40; H01Q 21/061; H01Q 23/00; H01Q 19/065; H01Q 1/2283; H01Q 1/247; H01Q 25/02; H01Q 5/28; H01Q 5/48; H01Q 7/00; H01Q 9/20; G06K 19/04
USPC .......................... 235/454, 486, 487, 492, 488
See application file for complete search history.

(56) References Cited

U.S. PATENT DOCUMENTS

| | | | |
|---|---|---|---|
| 4,155,793 | A | 5/1979 | Salemme et al. |
| 6,656,319 | B1 | 12/2003 | Boyd et al. |
| 6,818,276 | B2 | 11/2004 | Bourdelais et al. |
| 7,288,320 | B2 | 10/2007 | Steenblik et al. |
| 7,710,629 | B2 | 5/2010 | Palmateer |
| 7,917,298 | B1 | 3/2011 | Scher et al. |
| 8,113,427 | B2 | 2/2012 | Ross et al. |
| 2002/0068018 | A1 | 6/2002 | Pepper et al. |
| 2004/0026684 | A1 | 2/2004 | Empedocles |
| 2004/0066273 | A1 | 4/2004 | Cortina et al. |
| 2006/0231625 | A1 | 10/2006 | Cumming et al. |
| 2007/0212266 | A1 | 9/2007 | Johnston et al. |
| 2007/0281657 | A1 | 12/2007 | Brommer et al. |
| 2007/0285843 | A1 | 12/2007 | Tran |
| 2008/0024872 | A1 | 1/2008 | Dunn et al. |

(Continued)

OTHER PUBLICATIONS

International Search Report and Written Opinion for PCT/US2012/050744 dated Oct. 23, 2012.

(Continued)

*Primary Examiner* — Thien M Le
(74) *Attorney, Agent, or Firm* — Pepper Hamilton LLP

(57) ABSTRACT

A detectable taggant is described. The detectable taggant may include at least one nano-antenna having a resonant frequency of about 300 GHz to about 800 THz. The nano-antenna is adapted to be physically or chemically associated with an article of manufacture.

28 Claims, 3 Drawing Sheets

(56) References Cited

U.S. PATENT DOCUMENTS

| | | | |
|---|---|---|---|
| 2008/0150688 A1* | 6/2008 | Burr | 340/10.1 |
| 2008/0238627 A1* | 10/2008 | Oldham et al. | 340/10.1 |
| 2009/0039158 A1 | 2/2009 | Grishin et al. | |
| 2010/0148050 A1 | 6/2010 | Bari | |
| 2011/0003279 A1 | 1/2011 | Patel | |
| 2011/0198501 A1 | 8/2011 | Ouchi et al. | |
| 2011/0245460 A1 | 10/2011 | Livingston et al. | |
| 2011/0253744 A1 | 10/2011 | Pelfrey | |
| 2012/0055013 A1* | 3/2012 | Finn | 29/600 |
| 2012/0251125 A1* | 10/2012 | Harman | 398/135 |
| 2013/0278413 A1* | 10/2013 | Kamath et al. | 340/539.11 |
| 2014/0209691 A1* | 7/2014 | Finn et al. | 235/492 |

OTHER PUBLICATIONS

Balanis, Antenna Theory: Analysis and Design, 3$^{rd}$ Edition, Apr. 2005 (Abstract).

Berland, Photovoltaic Technologies Beyond the Horizon: Optical Rectenna Solar Cell, Final Report, *National Renewable Energy Laboratory* (*U.S. Department of Energy Laboratory*) (Aug. 1, 2001-Sep. 30, 2002), pp. 1-21.

Bharadwaj et al., Optical Antennas, *Advances in Opticals and Photonics* (Aug. 11, 2009), 1:438-483.

Biagioni et al., Nanoantennas for visible and infrared radiation, *Rep. Prog. Phys.* (2012), 75:024402-024442.

Choi et al., Fabrication of Conducting Polymer Nanowires, *Nanowires-Implementations and Applications* (Jul. 18, 2011), 19:440-454.

Cooper et al., THz Imaging Radar for Standoff Personnel Screening, *IEEE Transactions on Terahertz Science and Technology* (Sep. 2011), 1(1):169-182.

Dendrimer, http://en.wikipedia.org/wiki/Dendrimer (Printed from Internet Dec. 9, 2012).

Dong et al., Synthesis, Manipulation and Conductivity of Supramolecular Polymer Nanowires, *Chemistry—A European Journal* (Dec. 11, 2006), 13(3):822-828 (Absstract).

Grossman et al., Terahertz Imaging and Security Applications, National Institute of Standards & Technology, Quantum Electrical Metrology Division (Nov. 17, 2004).

Hannant et al., Modification of DNA-templated conductive, polymer nanowires via click chemistry, *Chemical Communications* (Jul. 13, 2010), 46:5870-5872 (Abstract).

Hirsch et al., Nanoshell-mediated near-infrared thermal therapy of tumors under magnetic resonance guidance, *PNAS* (Nov. 11, 2003), 100(23):13549-13554.

Jeon et al., Electrical characterization of conducting polypyrrole by THz time-domain spectroscopy, *Appl. Phys. Lett.* (2000), 77:2452-2454 (Abstract).

Lee et al., Self-Ordered, Controlled Structure Nanoporous Membranes Using Constant Current Anodization, *Nano Lett.* (Nov. 14, 2008), 8(12):4624-4629 (Abstract).

Moon et al., Fabrication of Highly Uniform Conductive Polypyrrole Nanowires with DNA Templates, *Journal of Nanoscience and Nanotechnology* (May 2010), 10(5):3180-3184 (Abstract).

Ohgai, Fabrication of Functional Metallic Nanowires Using Electrodeposition Technique, *Electrodeposited Nanowires and their Applications* (Feb. 1, 2010), 3:62-84.

Pastore et al., Fabrication of ultra thin anodic aluminium oxide membranes by low anodization voltages, *IOP Conf. Series: Materials Science and Engineering* (2011), 23:012025-012028.

Polycarbonate (PCTE) Membranes, http://www.sterlitech.com/membrane-disc-filters/polycarbonate-membranes.html (Printed from Internet Dec. 9, 2012).

Schreiber et al., DNA Origami-Templated Growth of Arbitrarily Shaped Metal Nanoparitces, *Small* (May 24, 2011), 7(13):1795-1799 (Abstract).

She et al., Electrodeposition of One-Dimensional Nanostructures, *Recent Patents on Nanotechnology* 2009), 3:182-191.

Shenoy et al., Surface functionalization of gold nanoparticles using hetero-bifunctional poly(ethylene glycol) spacer for intracellular tracking and delivery, *International Journal of Nanomedicine* (2006), 1(1):51-57.

Thermo Scientific, Tech Tip #2: Attach a protein onto a gold surface (2008).

Wang et al., The physical theory and propagation model of THz atmospheric propagation, *Journal of Physics: Conference Series* (2011), 276:012223-012233.

Williams JR. et al., Optically Coded Nanocrystal Taggants and Optical Frequency IDs, Proc. *SPIE 7673, Advanced Environmental, Chemical, and Biological Sensing Technologies VII*, 76730M (Apr. 24, 2010), pp. 1-14.

Engineers demonstrate first room-temperature semiconductor source of coherent Terahertz radiation, accessed at http://web.archive.org/web/20120730085014/http://m.phys.org_news130385859.html May 19, 2008 p. 2.

Faculteit Technische Natuurkunde Ultrabright THz source, accessed at http://web.archive.org/web/20111230114442/http://www.tue.nl/universiteit/faculteiten/faculteit-tn/onderzoek/onderzoekscluster-plasmas-en-straling/coherence-and-quantum-technology-cqt/research/laser-assisted-accelerators/ultrabright-thz-source, accessed on Oct. 20, 2015, pp. 1-5 (Oct. 29-Dec. 30, 2011).

Bernier et al., Terahertz encoding approach for secured chipless radio frequency identification, Journal of Applied Optics (Aug. 5, 2011), 50(23):4648-4655.

Boyle, Terahertz-Band Mobile Phones Could See Through Walls, accessed at http://web.archive.org/web/20120626110318/http://www.popsci.com.au/technology/terahertz-band-mobile-phones-could-see-through-walls, Apr. 19, 2012, pp. 1-3.

Courtland, A Cheap Terahertz Camera, accessed at http://web.archive.org/web/20120606044708/http://spectrum.ieee.org/semiconductors/optoelectronics/a-cheap-terahertz-camera, Apr. 2012, pp. 1-2.

Humpries, Future smartphone cameras to see through walls, accessed at http://web.archive.org/web/20120422045815/http://www.geek.com/articles/mobile/future-smartphone-cameras-to-see-through-walls-20120419, Apr. 19, 2012, pp. 1-5.

International Search Report and Written Opinion for PCT/US2013/039849 dated Oct. 23, 2012.

Lin et al., Smart temperature-controlled water vapor permeable polyurethane film, Journal of Membrane Science (May 4, 2007), 299(1-2):91-96.

Mayes, Miniature field deployable Terahertz source, Proceedings of the SPIE (May 19, 2006), 6212:1-11.

Dryness, Everything You Wanted to Know About Silica Gel but Didn't Know Who to Ask, Yahoo, accessed at https://web.archive.org/web/20130117065601/http://voices.yahoo.com/everything-wanted-know-silica-gel-but-3343922.html?, May 21, 2009, pp. 1-4.

THZ Materials, Tydex J.S.CO., accessed at http://web.archive.org/web/20110504082942/http://www.tydexoptics.com/pdf/THz_Materials.pdf, May 4, 2011, pp. 1-5.

Hamilton, Water Vapor Permeability of Polyethylene and Other Plastic Materials, The Bell System Technical Journal (Feb. 1967), 46(2):391-415.

What is Terahertz?, Teraview, accessed at https://web.archive.org/web/20140708002959/http://www.teraview.com/about/what-is-terahertz-thz.html, Apr. 17, 2012, p. 1.

* cited by examiner

FIGURE 3

310
Selecting at least one nano-antenna

320
Providing the nano-antenna

330
Disposing the nano-antenna on or in an article of manufacture

NANO-ANTENNA BASED INFRARED MOLECULAR TAGGANTS

CROSS-REFERENCE TO RELATED APPLICATIONS

This application is a U.S. national stage filing under 35 U.S.C. §371 of International Application No. PCT/US2012/050744, filed Aug. 14, 2012 and entitled "Nano-Antenna Based Infrared Molecular Taggants," the disclosure of which is incorporated by reference in its entirety.

BACKGROUND

An antenna is generally a transducer device that receives or transmits electromagnetic radiation. The frequency of radiation that may be received or transmitted by an antenna is dependent on the size of the antenna, the speed of light and the distance that electrons can travel (electron mobility) in the material medium of the antenna. Because electromagnetic waves propagate more slowly in a medium than in free space, the same number of waves will span a greater distance in free space than in the transmission medium, hence the transmission medium is said to have an electrical length that is greater than its physical length. Typically, the electrical length of an antenna is expressed in units of the wavelength (in the antenna medium) corresponding to the resonant frequency of the antenna.

Antennas are typically associated with signals having a frequency of about 30 kHz to about 30 GHz and may be associated with, for example, longwave AM radio broadcasting, RFID tags, wireless LAN, radars, and satellite television broadcasting. In general, the electrical length of an antenna is on the order of the free-space wavelength of the radiation at which the antenna is resonant. For example, a dipole antenna is typically about $\frac{1}{4}^{th}$ the free-space wavelength. Similarly, the physical length of an antenna is on the order of the wavelength in the antenna medium of the radiation at which the antenna is resonant. Given that the wavelength of electromagnetic radiation is shorter in a medium than in free space, the physical length of an antenna is typically shorter than its electrical length.

Every antenna has a characteristic impedance, which is the ratio of voltage to current at any given point in the antenna. In general, the impedance of an antenna is a complex number dependent on frequency of the voltage (or current). The real part of the complex impedance is pure resistance and is frequency independent. The complex part (also called reactance) is the frequency dependent part of the impedance and may be either directly proportional to the frequency (inductive reactance) or inversely proportional to the frequency (capacitive reactance). The resonant frequency of an antenna is defined as the frequency at which the capacitive impedance and the inductive impedance of the antenna are equal and opposite to each other, thereby cancelling each other and making the impedance at that frequency purely resistive. The voltage and current at this frequency are in phase with each other.

The complex impedance $Z_a$, of an antenna may be determined by the following formula:

$$Z_a = R_a + iX_a \qquad (1)$$

where $R_a$ is the resistance, and $X_a$ is the reactance of the antenna, having a capacitive component and an inductive component according to:

$$X_a = X_C + X_L = (-1/\omega C) + \omega L \qquad (2)$$

where $\omega = 2\pi f$ is the angular frequency, and f is the frequency. It is evident that by changing one or both of the inductive impedance $X_L$ and the capacitive impedance $X_C$ that the resonant frequency of an antenna can be changed.

For optical frequencies, ranging from terahertz to petahertz, metals are not perfect conductors but may be described as free-electron gases. Incident radiation at these frequencies is not perfectly reflected, but rather penetrates the metal surface and produces oscillations in the free-electron gas. Quantum effects apply at such frequencies, and surface plasmon resonances cause deviations in material properties. Classical antenna theory, therefore, needs to be modified by replacing classical impedance with local density of electromagnetic states (LDOS). The LDOS can be expressed in terms of Green's function tensor $\overleftrightarrow{G}$. For a quantum dipole $\vec{p}$ located at $\vec{r}_0$ the partial LDOS is expressed as:

$$\rho_p(\vec{r_0}, \omega) = \frac{6\omega}{\pi c^2} \left[ \vec{n_p} \cdot \text{Im}\{\overleftrightarrow{G}(\vec{r_0}, \vec{r_0}, \omega)\} \cdot \vec{n_p} \right], \qquad \text{Eq. (1)}$$

where $\vec{n_p}$ is the unit vector in the direction of the dipole $\vec{p}$, and $\omega$ is the angular frequency. The full LDOS can be obtained by averaging the partial LDOS of Eq. (1), and is expressed as:

$$\rho(\vec{r_0}, \omega) = \langle \rho_p(\vec{r_0}, \omega) \rangle \qquad \text{Eq. (2)}$$
$$= \frac{2\omega}{\pi c^2} \text{Im}[T_r(\overleftrightarrow{G}(\vec{r_0}, \vec{r_0}, \omega))],$$

where Tr denotes the trace.

By representing the quantum emitter as a classical dipole $\vec{p}$, located at $\vec{r}_0$, the power dissipated by the emitter at angular frequency $\omega$ is expressed as:

$$P = \frac{1}{2} \int_V \text{Re}\{\vec{j} \cdot \vec{E}\} dV \qquad \text{Eq. (3)}$$
$$= \frac{\omega}{2} \text{Im}\{\vec{p}^* \cdot \vec{E}(\vec{r_0})\}$$
$$= \frac{\pi \omega^2}{12 \varepsilon_0} |\vec{p}|^2 \rho_p(\vec{r_0}, \omega)$$

where, V is the source volume, $\vec{j}$ is the current density, and $\vec{E}$ is the electric field.

Using the expression for dipole radiation in free space: $P^0 = |\vec{p}|^2 \omega^4/(12\pi\varepsilon_0 c^3)$, LDOS in terms of normalized radiation can be expressed as:

$$\rho_p(\vec{r_0}, \omega) = \frac{\omega^2}{\pi^2 c^3} \frac{P}{P^0}. \qquad \text{Eq. (4)}$$

The antenna resistance can then be calculated as:

$$R = \frac{\pi}{12\varepsilon_0} \rho_p(\vec{r_0}, \omega). \qquad \text{Eq. (5)}$$

SUMMARY

In an embodiment, a detectable taggant for an article of manufacture may include at least one nano-antenna having a resonant frequency of about 300 GHz to about 800 THz. The nano-antenna may be adapted to be physically or chemically associated with an article of manufacture.

In an embodiment, a method of labeling an article of manufacture with a detectable taggant is described. The method may include disposing a detectable taggant which may include at least one nano-antenna having a resonant frequency of about 300 GHz to about 800 THz on or in the article of manufacture.

In an embodiment, a method of encoding information on or in an article of manufacture is described. The method may include selecting at least one nano-antenna having a resonant frequency of about 300 GHz to about 800 THz to encode the information, providing the nano-antenna, and disposing the nano-antenna on or in the article of manufacture.

In an embodiment, an article of manufacture is described. The article of manufacture may include a detectable taggant including at least one nano-antenna having a resonant frequency of about 300 GHz to about 800 THz. The nano-antenna may be physically or chemically associated with the article of manufacture.

BRIEF DESCRIPTION OF DRAWINGS

FIG. 3 depicts an illustrative method of encoding information on or in an article of manufacture according to an embodiment.

DETAILED DESCRIPTION

Figure 1:
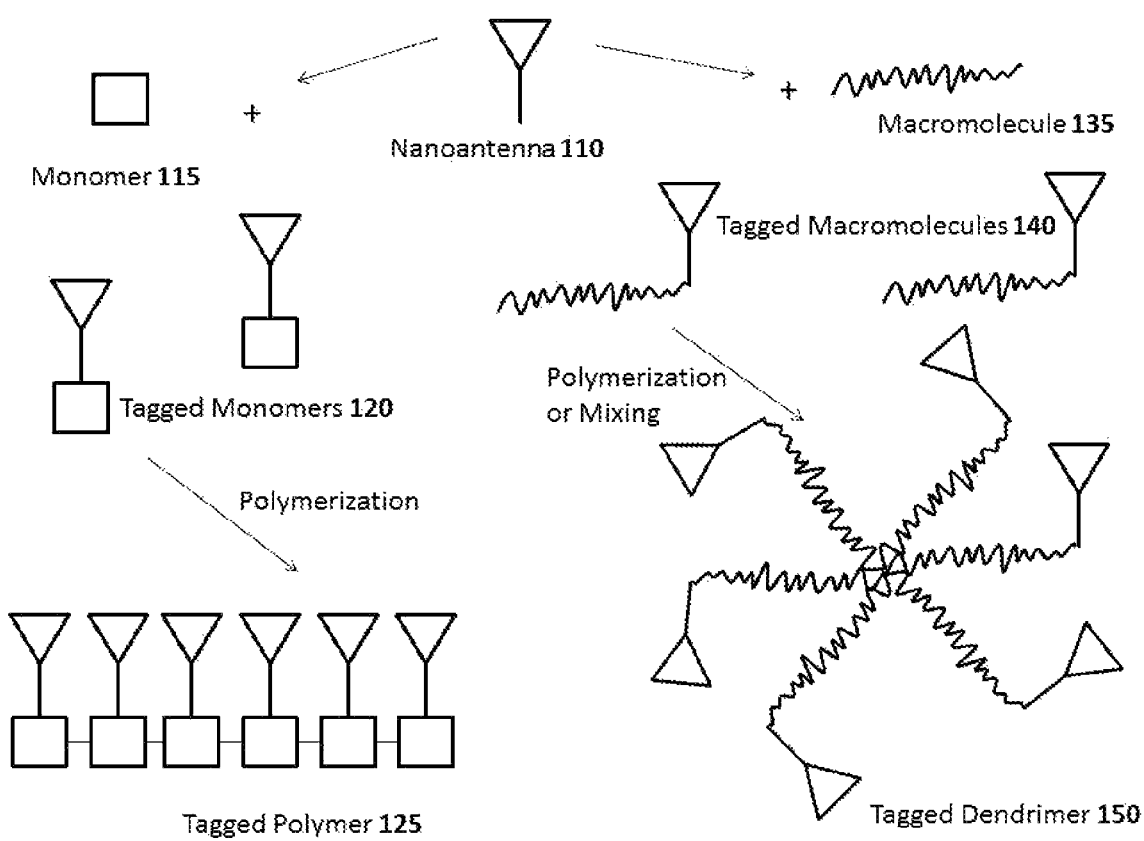
FIG. 1 depicts an illustrative schematic of conjugating a nano-antenna to a polymer according to an embodiment.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Millions of articles of manufacture constantly change hands during, for example, processing of raw materials, transportation, manufacturing, disposal of waste, and so forth. Identification and tracking of these articles of manufacture is a significant challenge. Bar-codes are the most common form of tagging used for identifying and tracking articles. However, barcodes convey very limited information because they encode a short bit string as a series of parallel bars in two colors. More recently, two dimensional (2D) matrices, commonly known as QR codes, have been developed and offer a significantly higher information density when compared to barcodes. The method of reading information from a barcode or a QR code requires the surface on which these codes are printed to be of a certain minimum size and essentially flat. This poses a serious limitation on the use of such codes.

Radio frequency (RF) tags have been used as alternatives to bar-codes and QR-codes. Typically, RF tags contain at least an integrated circuit that is used for storing the information, and an antenna resonating at radio frequencies for receiving and transmitting the stored information. The resonant frequency of the antenna within the RF tag determines the size, the range and the price of the tag. Lower frequency tags are typically inexpensive, but have relatively larger size and relatively shorter range, posing significant limitation in the use of RF tags.

A potential solution may be a tagging technology with antennas having resonant frequencies in the infra-red or optical (about 300 GHz to about 800 THz) region of the electromagnetic spectrum. Given that the wavelength for optical and far infrared frequencies is about 400 nm to about 1 μm, the required physical length of antennas resonating at optical and near infrared frequencies makes fabricating such antennas a significant challenge. Nanoscale fabrication coupled with suitable electrical shortening may provide a potential for creating nano-antennas resonating at optical and near infrared frequencies. Specific examples of resonant frequencies include about 300 GHz, about 400 GHz, about 500 GHz, about 600 GHz, about 700 GHz, about 800 GHz, about 900 GHz, about 1 THz, about 10 THz, about 50 THz, about 100 THz, about 150 THz, about 200 THz, about 250 THz about 300 THz, about 350 THz, about 400 THz, about 450 THz, about 500 THz, about 550 THz, about 600 THz, about 650 THz, about 700 THz, about 750 THz, about 800 THz, and ranges between any two of these values.

In some aspects, a detectable taggant is described. The detectable taggant may be made of at least one nano-antenna having a resonant frequency of about 300 GHz to about 800 THz is described. The nano-antenna may be adapted to physically or chemically associate with an article of manufacture.

In some embodiments, the nano-antenna may be in the form of a dipole, a monopole, an extra short dipole, a linear model, a Yagi-Uda array, a log-periodic array, a collinear array, or a combination thereof. In some embodiments, the nano-antenna may be a ½-wavelength dipole, a ¼-wavelength dipole, or an integer multiple of a ½-wavelength dipole.

In some embodiments, the nano-antenna may be molecularly associated with the article of manufacture so as to be a part of the material of manufacture of the article. In some embodiments, the nano-antenna may be chemically attached to the article of manufacture. The chemical conjugation may be by ionic, covalent, or non-covalent bonding.

Nano-antennas may be constructed from materials of appropriate length and geometry, and associated with an article of manufacture. In some embodiments, the nano-antenna may be made from a metal, a semi-metal, a conductor, a dielectric, a conducting polymer, a semiconductor, a carbon allotrope, a DNA molecule, a biomolecule, or any combination thereof. In some embodiments, the nanowires may have a diameter of about 1 nanometer (nm) to about 10 nm, about 10 nm to about 100 nm, about 100 nm to about 500 nm, or any combination thereof. In some embodiments, the length of the nanowires may be about 100 nm to about 500 nm, about 500 nm to about 1 μm, about 1 μm to about 10 μm, or any combination thereof. In some embodiments, the aspect ratio (ratio of length to diameter) of the nanowires may be about 5:1, about 7:1, about 10:1, about 12:1, about 15:1, about 17:1, about 20:1, about 25:1, or any range between any two of these values.

In some embodiments, the nano-antenna may be formed from metal nanowires. Examples of metals, not meant to be exhaustive, include gold, silver, platinum, palladium, copper, titanium, aluminum, cobalt, zinc, manganese, nickel, tantalum, iron, tungsten, chromium, molybdenum, niobium, cadmium, gallium, indium, lead, tin, alloys thereof, or any combination thereof.

Methods of fabricating metal nanowires of a given diameter and length are known in the art. For example, metal nanowires may be fabricated using lithographic steps. Metal thin films are deposited on a substrate, a suitable material that can resist an etchant of the metal is deposited on top of the metal thin film, nanowire patterns are drawn into the etch resistant material using a lithography step such that specific portions of the etch resistant material may be removed by a solvent while other portions are left behind, the metal is removed by a suitable process followed by removal of the etch resistant material to leave behind the metal nanowires. In some embodiments, the metal thin films may be deposited by, for example, chemical vapor deposition, sputtering, pulsed laser deposition, thermal evaporation, electron beam evaporation, and/or the like. In some embodiments, nanowires patterns are may be drawn by, for example, photolithography or electron beam lithography. In some embodiments, the metal may be removed chemically by dissolving in a suitable etchant. In some embodiments, the metal may be removed by exposing the metal to, for example, oxygen plasma, a beam of high energy electrons, a beam of high energy ions, ionized gas, and/or the like.

In some embodiments, the nanowires may be deposited by self-assembly, and in some embodiments, the nanowires may be deposited by precipitation from an appropriate solution. In some embodiments, the nanowires may be electrodeposited using molecular templates. The specific methods used for fabricating metal nanowires will depend on the particular metal being deposited. One of ordinary skill in the art will be able to choose an appropriate method of fabrication guided by factors such as the specific metal, the specific substrate on which the metal is being deposited, the cost of fabrication, the scalability of the process and/or the like.

In some embodiments, the nano-antenna may be conjugated to an article of manufacture by a thiol-containing moiety such as, for example, dithiobis(succinimidyl propionate), or a bi-functional poly(ethylene glycol)-thiol.

In some embodiments, the nano-antenna may be formed from a conducting polymer material. Examples of conducting polymers, not meant to be exhaustive, include polypyrroles, polyanilines, polythiophenes, polyfluorenes, polyphenylenes, polypyrenes, polyazulenes, polynaphthalenes, polycarbazoles, polyindoles, polyacetylenes, poly(p-phenylene vinylene)s, and/or the like.

Conducting polymer nanowires can be synthesized using a variety of methods known in the art. In some embodiments, the conducting polymer nanowires are formed by polymerizing corresponding monomers inside a nanoporous template followed by removal of the template. Examples of templates include, but are not limited to, nanoporous membranes of polycarbonate, nanoporous anodized aluminum oxide, nanoporous silica, and/or the like. The template may be removed by dissolving the template in an appropriate etchant. In some embodiments, the conducting polymers are formed by polymerizing corresponding monomers in the presence of surfactants or DNA molecules as templates. For example polyaniline nanowires can be synthesized by polymerization in the presence of β-naphthalene sulfonic acid or hexadecylmethylammonium chloride and polypyrrole nanowires can be synthesized by polymerization in the presence of surfactants such as cetyltrimethylammonium bromide, dodecyltrimethylammonium bromide, or ammonium persulfate. In some embodiments, the conducting polymer nanowires may be deposited using techniques such as electrospinning nanolithography, dip-pen nanolithography, electron-beam lithography, and so forth. It will be understood that the specific methods for synthesizing conducting polymer nanowires will depend on the specific choice of the conducting polymer used in the particular embodiment. A skilled artisan will be able to choose an appropriate method based on factors such as choice of conducting polymer, desired dimensions of the nanowires, the substrate material, compatibility of reagents and other synthesis conditions with the substrate material, and/or the like.

FIG. 1 depicts an illustrative schematic of conjugating a nano-antenna to a polymer according to an embodiment. In some embodiments, the nano-antenna 110 may be conjugated to a carrier particle. In some embodiments, the carrier particle may be part of, for example, a support material for manufacturing the article. In some embodiments, the carrier particle may be a linker between the nano-antenna and, for example, a material of manufacture of the article. The material of manufacture of the article may be, for example, a polymer, a metal, a biomolecule, a semiconductor, an insulator, and the like. In some embodiments, a nano-antenna 110 may be chemically conjugated with a monomer 115 to form a tagged monomer 120. Tagged monomers 120 may then be polymerized under appropriate conditions to form the tagged polymer 125. In some embodiments, the monomer 115 may be a monomer for producing polymers such as, for example, polycarbonates, polystyrenes, polyurethanes, polyimides, poly (ethylene terephthalate) polyethersulfone, and/or the like, such that the nano-antenna 110 is incorporated into the polymer that is used for producing an article of manufacture.

In some embodiments, the nano-antenna 110 may be chemically conjugated with a macromolecule 135 that may form a dendrimer such as, for example, poly(amidoamine), poly(propylene imine), an aromatic polyether dendrimer, a metallodendrimer, and/or the like to form a tagged dendrimer 150 upon mixing or polymerization under appropriate conditions. In some embodiments, the nano antennas 110 are conjugated with the capping amine 135 of the dendrimer using crosslinkers having a N-hydroxysuccinimide ester group such as, for example, dithiobis(succinimidyl propionate), disuccinimidyl suberate, bis(sulfosuccinimidyl) suberate, and/or the like, to form a tagged amine 140.

Figure 2:
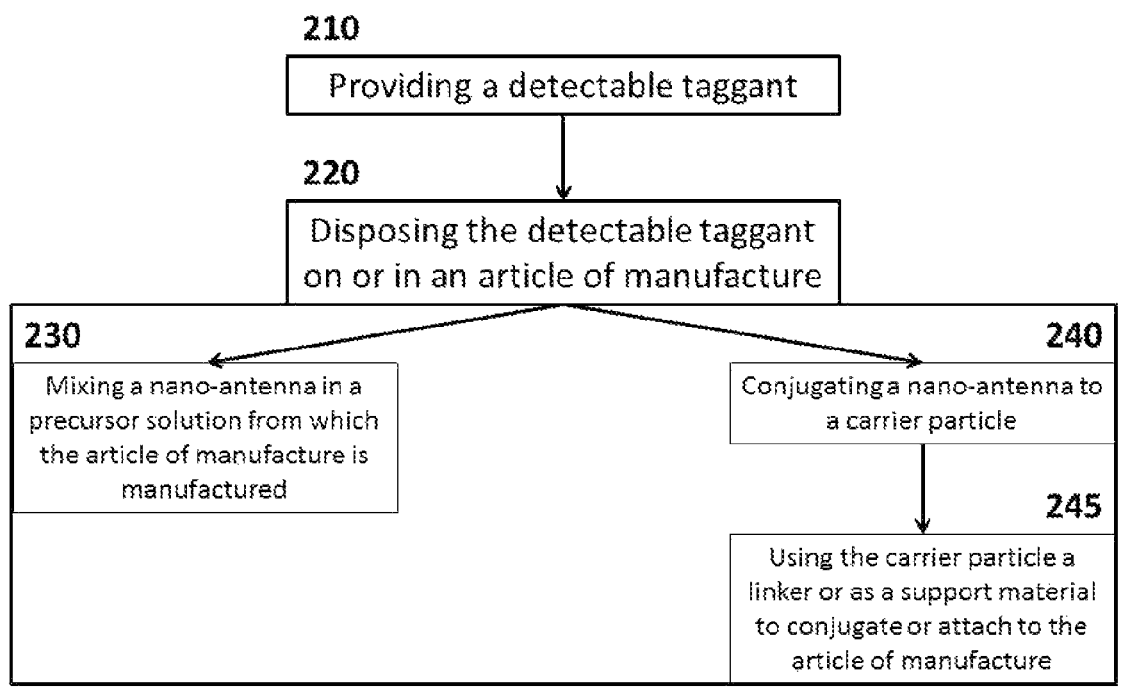
FIG. 2 depicts an illustrative method of labeling an article of manufacture with a detectable taggant according to an embodiment.

A detectable taggant such as described herein may be used as a label for an article of manufacture. FIG. 2 depicts a flow diagram for an illustrative method of labeling an article of manufacture with a detectable taggant according to an embodiment. In some embodiments, a method may include providing 210 a detectable taggant made of at least one nano-antenna having a resonant frequency of about 300 GHz to about 800 THz, and disposing 220 the nano-antenna on or in an article of manufacture. Various embodiments of the detectable taggant are described herein.

In some embodiments, disposing the nano-antenna may include physically or chemically associating the nano-antenna with the article of manufacture. In some embodiments, the nano-antenna may be conjugated 240 to a carrier particle. Examples of carrier particles may include, without limitation, fibers, microfibers, nanoparticles, nanowires, nanospheres, microparticles or microspheres of, for example, metals, semimetals, semiconductors, metal oxides, metal phosphates, metal carbonates, polymers, metal-coated polymers, carbon allotropes, doped metal oxides, aggregates of biomolecules, organo-metallic complexes, and/or the like. In some embodiments, the carrier particle may be a dendrimer such as, for example, poly(amidoamine), poly(propylene imine), aromatic polyether dendrimers, metallo-dendrimers, and so forth. In some embodiments, the carrier particle may be part of, for example, a support material 245 for manufacturing the article. In some embodiments, the carrier particle may be used as a linker 245 between the nano-antenna and, for example, a material of manufacture of the article. The material of manufacture of the article may include, without limitation, a polymer, a metal, a biomolecule, a semiconductor, an insulator, and so forth. A skilled artisan will readily recognize the various embodiments that may be combined.

In some embodiments, the nano-antenna, either with or without a carrier particle, may be mixed 230 in a precursor solution from which the article is manufactured. The article may be manufactured from a precursor solution having at least one monomer of at least one of the polymers that are used to manufacture the article. The nano-antenna may, in such embodiments, become part of the article of manufacture. In some embodiments, the nano-antenna may be about 0.01% to about 10% (by volume) of the precursor solution. Specific examples include about 0.01%, about 0.1%, about 1%, about 2.5%, about 5%, about 7.5%, about 10%, and ranges between any two of these values.

In some embodiments, the nano-antenna may be physically disposed on the article of manufacture. In some embodiments, the nano-antenna may be disposed on a film attached externally to the article. The film may be, for example, pasted, glued or laminated on to the article. In some embodiments, the nano-antenna, comprising nanowires of, for example, a metal, a metal oxide, a semiconductor, a conducting polymer, and/or the like, may be deposited directly on to the article of manufacture using techniques such as, for example, chemical vapor deposition, physical vapor deposition, electrodeposition, self-assembly, template assisted deposition, and/or the like. In some embodiments, biomolecules like, for example, DNA may act as templates for depositing the nano-antenna. In some embodiments, the nano-antenna may be, for example, stamped or printed on to the article of manufacture.

A nano-antenna in a detectable taggant may act as a strong absorber at the resonant frequency of the nano-antenna, thereby appearing black when irradiated at that frequency. One or more nano-antennas may be used to encode information on or in the article of manufacture. FIG. 3 depicts a flow diagram of an illustrative method of encoding information on or in an article of manufacture according to an embodiment. In some embodiments, the method may include selecting 310 at least one nano-antenna, having a resonant frequency from about 300 GHz to about 800 THz, providing 320 the nano-antenna and disposing 330 the nano-antenna on or in the article of manufacture.

Various embodiments for the nano-antenna, and for disposing the nano-antenna on or in an article of manufacture are described herein. One of ordinary skill in the art will be able to recognize the various embodiments that may be combined.

In some embodiments, information may be encoded as a set of frequencies that may be absorbed by an array of nano-antennas placed on the article. In some embodiments, information may be encoded as a position of the nano-antenna on the article of manufacture, a polarization of the nano-antenna, a specific spatial pattern of several nano-antennas on the article of manufacture, a frequency response of one or more nano-antennas, binary combinatorial binning of several nano-antennas, and so forth.

In some embodiments, encoded information may be retrieved, for example by irradiating the article of manufacture on which the detectable taggant is disposed. In some embodiments, the article may be irradiated with radiation of frequency of about 300 GHz to about 800 THz. In some embodiments, a single frequency radiation may be used to irradiate the article. In some embodiments, a single pulse of radiation, may be used to irradiate the article. In some embodiments, multiple pulses of radiation, of a single or multiple frequencies may be used to irradiate the article. In some embodiments, a pulse may last for a duration of about 1 picosecond (ps) to about 1 nanosecond (ns), about 1 ns to about 1 microsecond (µs), about 1 µs to about 1 millisecond (ms), about 1 ms to about 1 second (s), about 1 s to about 10 s, any range between any two of these values, or a combination thereof. In embodiments using multiple pulses, the pulses may be separated by a time of about 1 ps to about 1 ns, about 1 ns to about 1 µs, about 1 µs to about 1 ms, about 1 ms to about 1 s, about 1 s to about 10 s, any range between any two of these values, or a combination thereof.

Information encoded on an article of manufacture may be useful for numerous reasons. In some embodiments, the information may be used to track an article such as, for example, a waste article, a microchip, an article in transit during transportation, an electronic component, an article on an assembly line, and so forth. In some embodiments, the information may be used to direct an article towards a programmed destination. For example, for a machined part on an assembly line to be directed towards a specific location on a machine, or a piece of luggage to be directed towards a specific luggage belt at an airport, and so forth. In some embodiments, the information may be used for authentication of an article such as, for example, a currency note, an identification document, a confidential document, and so forth. A skilled artisan will be able envision other uses of information, so encoded, on an article of manufacture.

A skilled artisan will readily recognize the various embodiments that may be combined and may envision other ways in which information may be encoded. The present disclosure is not meant to be limited by the various ways and schemes of encoding, retrieving, and/or using the information.

In some aspects, articles of manufacture having a detectable taggant are described. The detectable taggant may have a nano-antenna, preferably having a resonant frequency of about 300 GHz to about 800 THz, such that the nano-antenna is physically or chemically associated with the article of manufacture. Examples, not meant to be exhaustive, of articles of manufacture having a detectable taggant include electronic components, coatings for electronic components, substrates for electronic components, identification documents, protective coatings for identification documents, currency bills, confidential documents, shipping containers, waste containers, items of luggage, machined parts, tags or labels for articles of manufacture, and so forth. A skilled artisan will be able to envision other articles of manufacture having a detectable taggant. The present disclosure is not meant to be limited by the specific articles of manufacture described herein.

In some embodiments, a system for detecting an article of manufacture may include disposing a detectable taggant having a plurality of nano-antennas on an article of manufacture, encoding information in or on the article of manufacture using the plurality of nano-antennas, and retrieving the encoded information. The nano-antennas preferably have a resonant frequency of about 300 GHz to about 800 THz. Various embodiments for the detectable taggants, the nano-antennas, the articles of manufacture, and methods of encoding and retrieving information are described herein.

Embodiments illustrating the method and materials used may be further understood by reference to the following non-limiting examples:

EXAMPLES

Example 1

Preparation of Half-Dipole Antenna

Gold nanowires with a diameter of 20 nm and a length of 600 nm are electrodeposited in ultrathin anodized aluminum oxide (AAO) (thickness of about 600 nm). The AAO is fabricated using oxalic acid anodization of aluminum. A thin layer (about 10 nm) of gold is deposited on one side of the AAO as an electrode. Gold is then electrodeposited into the AAO pores through the other side to form gold nanowires. Because the electrodeposition stops at the edge of the AAO layer, the length of gold nanowires may be changed by changing the thickness of the AAO. The AAO is then dissolved in an acid or base solution to separate the gold nanowires. As half-dipole antennas, these had a resonant frequency of about 167 THz (free-space wavelength of 1.8 μm).

Example 2

Preparation of Full-Dipole Antenna

A polycarbonate membrane having a thickness of about 1.2 μm is fabricated by spin coating a polycarbonate solution and evaporating the solvent. A thin layer of gold is deposited on one side of the membrane and gold is electrodeposited through the other side. The membrane is then dissolved (in an organic solvent such as chloroform) to separate the gold nanowires which resonate at about 167 THz as full-dipole antennas.

The length, and thereby the resonant frequency of the gold nanowires may be changed by changing the thickness of the polycarbonate membrane.

Example 3

Tagging a Nano-Antenna

Gold nanowires are associated with a polymer using a bi-functional PEG-thiol. The thiol-end is bound to the gold nanowires while the other functional group is bound to a polymer from which an article is manufactured. Gold, being inert, does not alter the chemical properties of the polymer and is also resistant to corrosion.

It is to be noted that similar processes may be used for making nano-antennas from other metals listed herein and associating the nano-antennas with articles of manufacture.

Example 4

Nano-Antennas Made from Conducting Polymers

For a conducting polymer nano-antenna to resonate at about 167 THz (1.8 μm free-space wavelength), the length of the nano-antenna is calculated to be about 38.5 nm.

DNA molecules with appropriate number of base pairs (in this case, about 58 base pairs) are used as templates of appropriate length for depositing polypyrrole on (3-aminopropyl) triethoxysilane (APTES) modified silicon substrates using ammonium persulfate as an oxidant. Alternatively, mica may be used as a substrate.

Example 5

Preparation of Nano-Antennas with Dendrimers as Carrier Particles

Ethylenediamine is conjugated to a gold nano-antenna described earlier using dithiobis(succinimidyl propionate) (DSP) as a linker. The nano-antenna is attached to the DSP molecule via thiol linkage. The succinimidyl end of DSP has a high affinity to the amine group of the ethylenediamine covalently attached the nano-antenna to the ethylenediamine. Nano-antenna attached diamines are substituted in place of ethylenediamines used in formation of poly(amidoamine) dendrimer to form gold nano-antenna containing dendrimers.

Example 6

Method of Encoding Information on an Article of Manufacture

Nano-antennas absorb the radiation at their resonance frequency making them detectable by the absence of that frequency in the reflected light. This property is used for encoding information on an article of manufacture. Nano-antennas with a resonance frequency of about 167 THz are disposed on a piece of plastic in the pattern of a bar-code encoding a destination for a piece of luggage. The piece of plastic is glued on to the piece of luggage. The piece of plastic is irradiated optical light and frequencies of the reflected light are scanned. The information encoded by bar-code is revealed by the absence of light at 167 THz in the bar-code pattern.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A detectable taggant comprising:
    at least one nano-antenna having a resonant frequency of about 300 GHz to about 800 THz (far infrared to optical),
    wherein the nano-antenna is adapted to be physically or chemically associated with a radio frequency tag by a thiol-containing moiety.

2. The detectable taggant of claim 1, wherein an architecture of the nano-antenna comprises a dipole, a monopole, a linear model, Yagi-Uda type, a log-periodic array, a collinear array, an extra short dipole, or a combination thereof.

3. The detectable taggant of claim 1, wherein the nano-antenna is chemically conjugated to the radio frequency tag by non-covalent, covalent, or ionic bonding.

4. The detectable taggant of claim 1, wherein the nano-antenna comprises a metal, a semi-metal, a conductor, a dielectric, a conducting polymer, a semiconductor, a carbon allotrope, a DNA molecule, a biomolecule, or a combination thereof.

5. The detectable taggant of claim 1, wherein the nano-antenna comprises a metal nanowire.

6. The detectable taggant of claim 5, wherein the nanowire has a diameter of about 1 nm to about 500 nm.

7. The detectable taggant of claim 5, wherein the nanowire has a length of about 100 nm to about 10 μm.

8. The detectable taggant of claim 5, wherein the metal nanowire comprises one or more of gold, silver, platinum, palladium, copper, titanium, aluminum, cobalt, zinc, manganese, nickel, tantalum, iron, tungsten, chromium, molybdenum, niobium, cadmium, gallium, indium, lead, tin, and alloys thereof.

9. The detectable taggant of claim 1, wherein the nano-antenna is adapted to be conjugated to a carrier particle.

10. The detectable taggant of claim 9, wherein the carrier particle is used as a support material or as a linker to conjugate the nano-antenna to the radio frequency tag.

11. The detectable taggant of claim 9, wherein the carrier particle is a dendrimer.

12. A method of labeling a radio frequency tag with a detectable taggant, the method comprising:

providing a detectable taggant comprising a nano-antenna, wherein the nano-antenna has a resonant frequency of about 300 GHz to about 800 THz; and disposing the taggant on or in the radio frequency tag, wherein the nano-antenna is adapted to be associated with the radio frequency tag by a thiol-containing moiety.

13. The method of claim 12, wherein disposing the taggant comprises physically or chemically associating the nano-antenna with the radio frequency tag.

14. The method of claim 12, further comprising mixing the nano-antenna in a precursor solution from which the radio frequency tag is manufactured.

15. The method of claim 12, further comprising chemically conjugating the nano-antenna to the radio frequency tag by non-covalent, covalent, or ionic bonding.

16. The method of claim 12, wherein providing the detectable taggant comprises the nano-antenna selected from a metal, a semi-metal, a conductor, a dielectric, a conducting polymer, a semiconductor, a carbon allotrope, a DNA, a biomolecule, and a combination thereof.

17. The method of claim 12, wherein providing the detectable taggant comprises synthesizing the nano-antenna by electrodeposition assisted by a template.

18. The method of claim 12, further comprising conjugating the nano-antenna to a carrier particle prior to disposing the taggant.

19. The method of claim 18, further comprising conjugating the nano-antenna to the radio frequency tag by using the carrier particle as a support material or as a linker.

20. A method of encoding information on or in a radio frequency tag, the method comprising:
    selecting at least one nano-antenna to encode the information, wherein the nano-antenna has a resonant frequency of about 300 GHz to about 800 THz;
    providing the nano-antenna; and
    disposing the nano-antenna on or in the radio frequency tag, wherein the nano-antenna is adapted to be associated with the radio frequency tag by a thiol-containing moiety.

21. The method of claim 20, wherein disposing the nano-antenna comprises physically or chemically associating the nano-antenna with the radio frequency tag.

22. The method of claim 20, wherein selecting at least one nano-antenna comprises the information is encoded as a function of the properties the nano-antenna selected from spatial location, resonance frequency, frequency response, gain, polarization, and any combination thereof.

23. The method of claim 20, further comprising retrieving the information by irradiating the radio frequency tag with radiation of at least one frequency from about 300 GHz to about 800 THz.

24. The method of claim 20, further comprising using the information for tracking the radio frequency tag, authenticating the radio frequency tag, or recycling the radio frequency tag.

25. The method of claim 20, further comprising encoding the information using binary combinatorial binning.

26. The method of claim 20, further comprising encoding the information using specific spatial patterns.

27. The method of claim 20, further comprising encoding the information using directional patterns or polarization patterns.

28. A system of detecting a radio frequency tag comprising:
    a detectable taggant comprising a plurality of nano-antennas having a resonance frequency of about 300 GHz to about 800 THz on the radio frequency tag,
    wherein information is encoded on the detectable taggant using at least one property of the plurality of nano-antennas;
    disposing the detectable taggant on the radio frequency tag, wherein the nano-antenna is adapted to be associated with the radio frequency tag by a thiol-containing moiety; and
    retrieving the information encoded on the detectable taggant.

* * * * *